US012788275B2

(12) United States Patent
Pool

(10) Patent No.: US 12,788,275 B2
(45) **Date of Patent: *Nov. 10, 2026**

(54) DEVICES AND METHODS FOR NON-INVASIVE IMPLANT LENGTH SENSING

(71) Applicant: NuVasive Specialized Orthopedics, Inc., San Diego, CA (US)

(72) Inventor: Scott Pool, Laguna Hills, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/222,193

(22) Filed: May 29, 2025

(65) Prior Publication Data

US 2025/0288221 A1 Sep. 18, 2025

Related U.S. Application Data

(60) Continuation of application No. 18/644,823, filed on Apr. 24, 2024, now Pat. No. 12,318,187, which is a division of application No. 17/819,338, filed on Aug. 12, 2022, now Pat. No. 11,980,458, which is a continuation of application No. 16/923,733, filed on Jul. 8, 2020, now Pat. No. 11,445,939, which is a continuation of application No. 13/253,065, filed on Oct. 4, 2011, now Pat. No. 10,743,794.

(51) Int. Cl.

| | |
|---|---|
| ***A61B 17/02*** | (2006.01) |
| ***A61B 5/00*** | (2006.01) |
| ***A61B 5/107*** | (2006.01) |
| *A61B 5/053* | (2021.01) |

(52) U.S. Cl.

CPC .......... *A61B 5/1076* (2013.01); *A61B 5/6878* (2013.01); *A61B 17/025* (2013.01); *A61B 5/0031* (2013.01); *A61B 5/053* (2013.01)

(58) Field of Classification Search

CPC .......... A61B 17/025; A61B 2017/0256; A61B 2017/0268; A61B 2017/0275; A61B 5/6878; A61B 5/0031; A61B 5/053; A61B 5/1076

See application file for complete search history.

(56) References Cited

U.S. PATENT DOCUMENTS

2010/0217271 A1* 8/2010 Pool .................. A61B 17/7216 606/264

* cited by examiner

*Primary Examiner* — Samuel S Hanna

(57) ABSTRACT

A device for the non-invasive sensing of the length of an implantable medical device includes an implantable medical device having first and second portions moveable relative to one another and a layer of resistive material disposed on one of the first and second portions. A contact is disposed on the other of the first and second portions, the contact being in sliding contact with the layer of resistive material upon relative movement between the first and second portions. A circuit is configured to measure the electrical resistance along a path including a variable length region of the layer of resistive material and the contact. The electrical resistance can then be converted into a length.

20 Claims, 12 Drawing Sheets

DEVICES AND METHODS FOR NON-INVASIVE IMPLANT LENGTH SENSING

RELATED APPLICATIONS

The present application is a continuation application of U.S. patent application Ser. No. 18/644,823, filed on Apr. 24, 2024 (published as U.S. Pat. Pub. No. 2024-0277257), which is a divisional application of U.S. patent application Ser. No. 17/819,338 filed on Aug. 12, 2022 (now U.S. Pat. No. 11,980,458), which is a continuation of U.S. patent application Ser. No. 16/923,733, filed Jul. 8, 2020, which is a continuation of U.S. patent application Ser. No. 13/253,065 filed Oct. 4, 2011 (now U.S. Pat. No. 10,743,794 issued Aug. 18, 2020), the contents of each of which are hereby incorporated by reference their entireties for all purposes.

FIELD OF THE INVENTION

The field of the invention generally relates to implantable medical devices and more particularly, implantable medical devices that undergo changes in length.

BACKGROUND

A variety of medical devices exist that are implanted inside the body and undergo a dimensional change. For example, a bone lengthening device is one type of implantable device that is typically inserted into first and second portions of a severed or broken bone. The device is then periodically lengthened to distract or grow the bone over a period of time. Such adjustments made to the bone lengthening device may be invasive or even non-invasive. As another example, growing rods or distraction devices may be secured to a subject's spine. These devices may be used to correct a medical condition such as scoliosis. In still other applications, these devices may be used to increase the distance between adjacent vertebrae to reduce symptoms associated with lumbar spinal stenosis or pinched nerves. Other bones such as the jaw bone may include an implantable medical device that is configured to elongate over time.

Regardless of the nature in which the implanted medical device is used, there often is a need to determine the absolute length of the implant as it exists inside the patient at any given moment. As an example, after the implanted medical device has undergone a length adjustment there is a need to determine whether or not the desired quantity of lengthening was indeed achieved. In addition, devices may change dimensions after the adjustment has been made (whether manual or non-invasive). For example, normal physiological movement of the subject may cause additional shortening or lengthening of the device after adjustment of the device. In these instances, it would be beneficial to know the actual length of the device in between adjustment procedures. For example, a physician might want to know if the device has strayed too far in either direction to warrant an additional adjustment.

U.S. Patent Application Publication No. 2010/0094302 discloses a non-invasive medical implant device that uses microphone sensor on an external adjustment device to sense when an internally-located magnet is undergoing rotation. Specifically, the microphone sensor picks up an acoustic signal (e.g., click) that is periodically generated by rotation of an internal magnet that is part of the implantable medical device. By counting the number of clicks, the external adjustment device can then translate this into an estimated length of the device. While such a method does provide a means to determine the length of the implanted medical device there is the possibility that one or more of the click signals may not be detected by the external adjustment device. In this instance, the actual length of the implanted medical device may then be different from the length that is calculated or otherwise determined by the external adjustment device. Further, while the external adjustment device may store the most current length of the device as determined by the sensed signals, it is possible that the subject may return to a different physician for his or her next adjustment procedure. Unless the size of the implanted medical device is stored locally on or with the patient (e.g., RFID or a card carried by the patient), the next physician will not know the most recent sizing of the device. Moreover, as stated above, there is the possibility that the implanted device may change lengths in between adjustment procedures. There thus is a need for methods and devices that will determine the absolute length of an implantable medical device at any given movement.

SUMMARY

In one embodiment of the invention, a device includes an implantable medical device having first and second portions moveable relative to one another and a layer of resistive material disposed on one of the first and second portions. The device includes a contact disposed on the other of the first and second portions, the contact being in sliding contact with the layer of resistive material upon relative movement between the first and second portions and a circuit configured to measure the electrical resistance along a path including a variable length region of the layer of resistive material and the contact.

In another embodiment of the invention, a method of sensing the length of an implantable medical device having first and second portions moveable relative to one another is disclosed. The implantable medical device includes a resistive pathway on one of the first and second portions of the implantable medical device along with a contact disposed on the other of the first and second portions, the contact being in sliding contact with the resistive pathway upon relative movement between the first and second portion. The electrical resistance along a path including a variable length region of the resistive pathway and the contact is measured. The measured electrical resistance is then converted to a length.

In another embodiment, a device includes an implantable medical device having first and second portions moveable relative to one another and a primary drive coil surrounding a segment of the implantable medical device containing both the first and second portions. At least one secondary coil surrounds a segment of the implantable medical device containing both the first and second portions. The device includes a first circuit configured to apply a drive voltage to the primary drive coil and measure signals in the at least one secondary coil and output a signal indicative to the length of the implantable medical device.

In another embodiment, a method of sensing the length of an implantable medical device having first and second portions moveable relative to one another includes applying a driving voltage to a primary drive coil surrounding a segment of the implantable medical device containing both the first and second portions. Signals in at least one secondary coil surrounding a segment of the implantable medical device containing both the first and second portions are measured and converted to a length.

In another embodiment, a device includes an implantable medical device having first and second portions moveable relative to one another, wherein the first and second portions are separated from one another by a dielectric material. The device includes an implantable resonant coil coupled to the first and second portions and an externally located drive coil operatively coupled to a signal generator. A frequency analyzer is operatively coupled to the drive coil configured to detect the resonant frequency of the implantable medical device, wherein said resonant frequency varies depending on the degree of relative orientation between the first and second portions.

In another embodiment a method of sensing the length of an implantable medical device having first and second portions moveable relative to one another includes providing an implantable medical device wherein the first and second portions are coupled to an implanted resonant coil. An external drive coil is driven adjacent to the implanted resonant coil with a signal generator at different frequencies. A resonant frequency of the implantable medical device is detected and the resonant frequency of the implantable medical device is converted to a length.

In another embodiment, a device includes an implantable medical device having first and second portions moveable relative to one another and an elongate member having first and second ends, the first end being secured to the first portion of the implantable medical device, the second end having secured thereto a magnet. The device includes a fulcrum on the second portion of the implantable medical device and contacts various points along the elongate member in response to relative movement of the second member relative to the first member. An externally located magnetic field source is configured to apply an oscillating magnetic field in proximity to the magnet secured to the elongate member. In another embodiment, a method of sensing the length of an implantable medical device includes providing an implantable medical device having first and second portions moveable relative to one another, an elongate member having first and second ends, the first end being secured to the first portion of the implantable medical device, the second end having secured thereto a magnet, and a fulcrum on the second portion of the implantable medical device and in contact with various points along the elongate member in response to relative movement of the second member relative to the first member. An oscillating magnetic field is applied at different frequencies in proximity to the magnet with an externally located magnetic field source driven by a power source. The power source for the externally located magnetic field source is monitored wherein the resonant frequency of the elongate member is determined based at least in part on the current draw of the power source. The resonant frequency of the elongate member is then converted to a length.

DETAILED DESCRIPTION OF THE ILLUSTRATED EMBODIMENTS

Figure 1A:
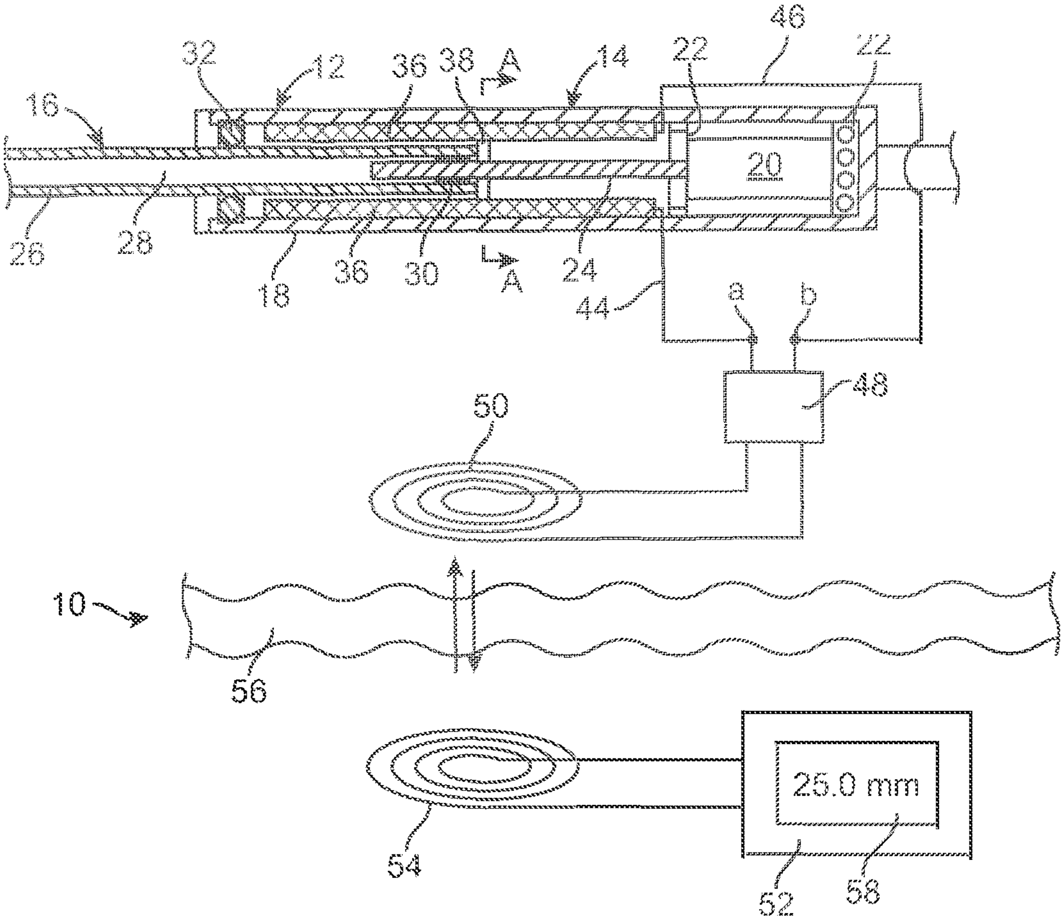
FIG. 1A illustrates a device that non-invasively measures the length of an implantable medical device according to one embodiment.

FIG. 1A illustrates a device 10 that non-invasively measures the length of an implantable medical device 12. The implantable medical device 12 may include any number of implantable medical devices 12 including those used to lengthen or distract bone or other tissue. These include, by way of example, distraction devices for use in bone lengthening applications (e.g., limb lengthening), spinal distraction devices for the treatment of scoliosis, spinal devices for the treatment of lumbar spinal stenosis, dental devices, and the like. The implantable medical device 12 may be one that is adjusted manually or more preferably, non-invasively. Still referring to FIG. 1A, the implantable medical device includes a first portion 14 and a second portion 16 that are moveable relative to one another. During use, the first portion 14 and second portion 16 move apart from one another for distraction or lengthening. Conversely, the first portion 14 and the second portion 16 may move toward one another for adjustment purposes or even to reduce lengthening or distraction forces. As seen in FIGS. 1A-IC, the first and second portions 14, 16 move in a telescopic fashion. In other alternative embodiments, however, the first and second portions 14, 16 do not need to be fashioned to move relative to one another in a telescopic manner. During implantation, the first portion 14 is typically secured to a first location (e.g., bone) while the second portion 16 is secured to a second, different location (e.g., different bone). Various fixation devices such as screws, pins, hooks, articulating joints, and the like may be used to secure one or both ends of the first and second portions 14, 16. In other embodiments, such as limb lengthening applications, a cavity, which may be natural or formed inside the bone, is used to receive one or both of the first and second portions 14, 16. The first and second portions 14, 16 may be secured using a mechanical fastener, cement, or method commonly known to those skilled in the art.

In the embodiment illustrated in FIGS. 1A-IC, the first portion 14 is a housing 18 in the shape of a tube or the like and is made from a biocompatible metal such as titanium. The housing 18 includes therein a permanent magnet 20 that is configured for rotational movement relative to the housing 18. The permanent magnet 20 may be formed from a rare earth magnet such as Neodymium-Iron-Boron. The permanent magnet may be made from a grade of N35 or higher, for example a grade of N50. One or more bearings 22 may be used to retain the permanent magnet 20. A lead screw 24 is connected either directly or indirectly via gears or the like (not shown) to the permanent magnet 20. Thus, rotational movement of the permanent magnet 20 causes rotational movement of the lead screw 24.

The second portion 16 of the implantable medical device 12 is in the form of a rod 26 that includes a hollow segment 28 that is dimensioned to receive the lead screw 24. A nut 30 is located within the hollow segment 28 and has threading that interfaces with threads located on the lead screw 24. Rotation of the lead screw 24 in a first direction thus causes the rod 26 to telescope into the housing 18 thus shortening the overall length of the implantable medical device 12. Conversely, rotation of the lead screw 24 in a second, opposite direction causes the rod 26 to telescope out of the housing 18 thus lengthening the overall length of the implantable medical device 12. A seal 32 is provided between the rod 26 and the housing 18 such that fluids and material remain external to the rod 26 and housing 18 during movement.

Figure 2A:
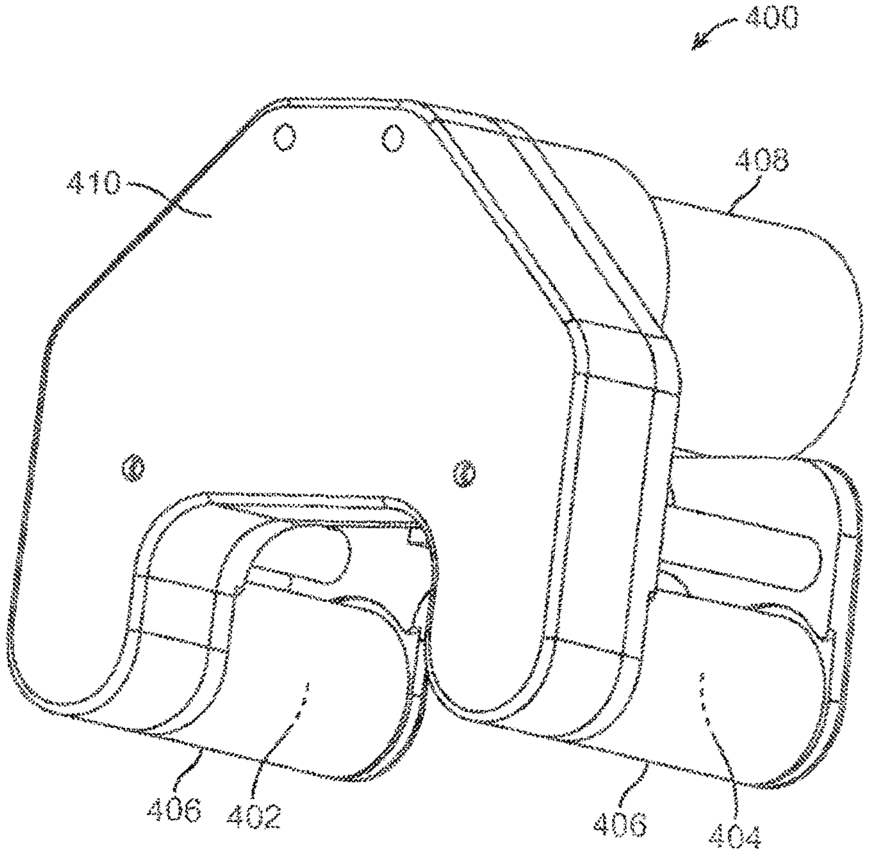
FIG. 2A illustrates a perspective view of an external adjustment device.
Figure 2B:
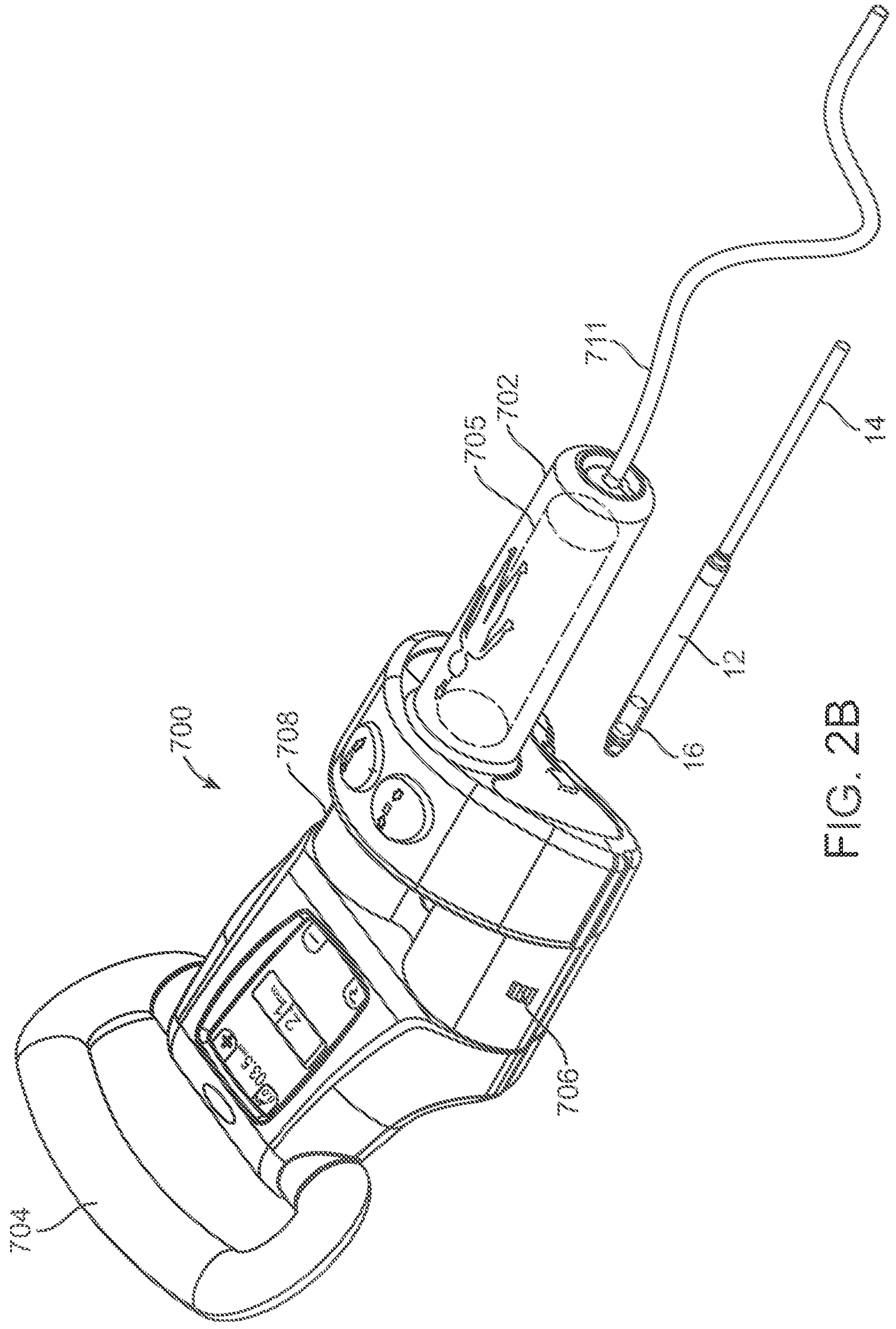
FIG. 2B illustrates a perspective view of an external adjustment device according to another embodiment.

Rotation of the permanent magnet 20 is accomplished by application of a moving magnetic field from a location external to the subject having the implantable medical device. The moving magnetic field is typically applied using an external adjustment device that has one or more rotating magnets that generate the driving magnetic field. Particular details on the nature of the external adjustment devices that can be used in connection with the distraction devices described herein are disclosed, for example, in U.S. Patent Application Publication Nos. 2009/0112207, 2010/0094302, 2010/0 121323, and U.S. patent application Ser. No. 13/172, 598, all of which are incorporated by reference herein. FIG. 2A illustrates an external adjustment device 400 according to one embodiment that includes two permanent magnets 402, 404 contained within respective covers 406. Each permanent magnet 402, 404 is rotatable within its respective cover 406 and provides a moving magnetic field. A motor 408 is mechanically engaged to the permanent magnets 402, 404 via a transmission (not shown) contained within a housing 410 of the external adjustment device 400. FIG. 2B illustrates another embodiment of an external adjustment device 700. The external adjustment device includes a first handle 702 and a second handle 704. Like the prior embodiment, there are two permanent magnets 706, 708 that are rotatable and provide a moving magnetic field. A power cord 711 supplies power to a motor 705 that drives the permanent magnets 706, 708 via a gear box (not shown). Additional details regarding external adjustment device 700 may be found in U.S. application Ser. No. 13/172,598 which is incorporated by reference herein.

Figure 1B:
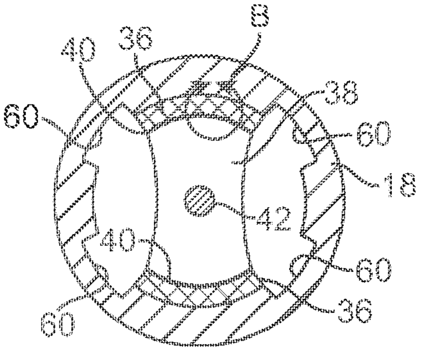
FIG. 1B illustrates a full sectional view of the device of FIG. 1A taken along the line A-A.

Referring back to FIGS. 1A-IC, the housing 18 includes a layer of resistive material 36 on an inner surface thereof. As best seen in FIGS. 1A and 1B, the housing 18 includes two separate layers of the resistive material 36 on generally opposing interior surfaces of the housing 18. It should be understood, however, that a single layer of resistive material 36 may suffice. Similarly, there may be more than two layers of resistive material 36. The layer of resistive material 36 may include any number of materials known to have a degree of electrical resistance. Exemplary materials include, for example, carbon although other known electrically resistive materials will work. Generally, in order to increase the resolution of the device 10, the resistive material 36 should have a relatively high degree of electrical resistance so that small changes in length will correspond to larger resistance differentials. An electrically conductive contact 38 is secured to the end of the rod 26. The contact 38 thus moves in conjunction with the rod 26 upon actuation of the permanent magnet 20. The contact 38 includes contact surfaces 40 that physically touch the resistive material 36. The contact surfaces 40 may include an edge, brushes, or rollers that contact the layer of resistive material 36. In this regard, the contact 38 forms part of the electrical circuit for measuring the resistance of the implantable medical device 12. Depending on the location of the rod 26, the actual length of the resistive material 36 within the electrical circuit varies. Thus, when the rod 26 is extended outward with respect to the housing 18 a larger portion of the resistive material 36 is part of the resistance circuit and resistance measurements via the circuit (discussed below in more detail) are higher. Conversely, when the rod 26 is collapsed inside the housing 18 a smaller portion of the resistive material 36 is part of the resistance circuit and resistance measurements via the circuit are lower. The contact 38 includes an aperture 42 therein for passage of the lead screw 24.

As seen in FIG. 1A, electrical conductors 44, 46 electrically connect to the two respective layers of resistive material 36. These electrical conductors 44, 46 connect to a circuit 48 which may be implemented in a microprocessor or the like. For example, the circuit 48 may include one or more processors configured to read and process measured resistance values at points a and b of the circuit in FIG. 1A. The circuit 48 may also optionally include memory for storing data therein. The memory may comprise an RFID chip. The data may include, for example, resistance values or corresponding data as well as calibration data unique to the particular implantable medical device 12. The circuit 48 is coupled to an antenna 50 which enables the circuit 48 to transmit data and other information to an externally located controller 52. The externally located controller 52 includes an antenna 54 and acts as a receiver to receive data communicated from the circuit 48. Thus, the circuit 48 acts as a transmitter while the controller 52 acts as a receiver. In one aspect of the invention, the controller 52 both powers and communicates digitally with the circuit 48. In this regard the circuit 48 does not need its own power source as the circuit 48 is powered inductively via the external controller 52. As seen in FIG. 1A, the communication occurs across the skin 56 of the subject.

The controller 52 includes a display 58 that is used to display one or more parameters indicative of the length of the implantable medical device 12. This can include a numerical value corresponding to the absolute length of the implantable medical device 12. The display 58 may also include a graphical representation of the device length (e.g., bar graph or the like) or other indicia of length. The controller 52 may also display the resistance value measured by the circuit 48.

FIG. 1B illustrates an optional feature wherein a plurality of longitudinal grooves 60 are disposed along an inner surface of the housing 18. The rod 26 includes corresponding protrusions (not shown) that form a splined tip that interfaces with the corresponding grooves 60. The tight tolerance of the splined tip with the grooves 60 keeps the rod 26 centered within the housing 18. Further, the combination of the splined tip and the grooves 60 act as an anti-rotation feature that prevents the rod 26 from rotating relative to the housing 18. Additional details regarding this optional aspect may be found in U.S. Patent Application Publication No. 2010/0217271 which is incorporated herein by reference.

Figure 1C:
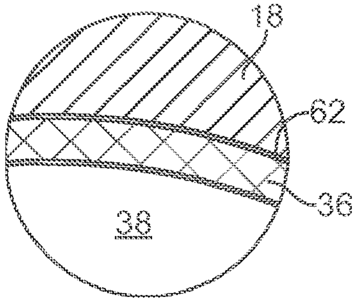
FIG. 1C illustrates view B of FIG. 1B.

FIG. 1C illustrates an enlarged view of detail B of FIG. 1B. As seen in FIG. 1C, the layer of resistive material 36 may be disposed on an insulation layer 62. The insulation layer 62 electrically insulates the layer of resistive material 36 from the underlying metallic housing 18. The insulation layer 62 may include a thin oxide layer that is formed by anodization.

To use the device 10, the external adjustment device 400 is placed near or adjacent to the patient's skin 56 near the location of implantable medical device 12. Activation of the external adjustment device 400 causes the two permanent magnets 402, 404 to rotate thereby causing the permanent magnet 20 to rotate along with the lead screw 24. Depending on the direction of rotation, the rod 26 either extends from or retracts into the housing 18. The actual length of the implantable medical device 12 is determined by measuring the resistance at points a and b using the circuit 48. The resistance measured at points a and b varies depending on the position of the contact 38 on the layer of resistive material 36. As the contact 38 moves away from the permanent magnet 20 additional resistance is added to the electrical pathway because of the additional resistive material 36 that is present in the electrical circuit. The circuit 48 measures this resistance value wherein it can be stored in the circuit 48 for later transmission or, alternatively, the resistance value may be directly transmitted to the controller 52. For example, in one aspect of the invention, when the circuit 48 is powered inductively via the external controller 52, one or more resistance measurements are made by the circuit 48 and this information is then transmitted wirelessly to the controller 52. The controller 52 can then take this data (e.g., resistance data) and convert the same to a length. For example, the controller 52 may include calibration data (calibration curve, look-up table, or the like) that is used to translate a resistance value into a length. The length can then be displayed on the display 58. The calibration data may be communicated from the circuit 48 or it may have already been pre-loaded into the controller 52. In addition, it is possible that the circuit 48 itself translates the resistance reading into a length and data corresponding to a length is transmitted to the controller 52.

Figure 1D:
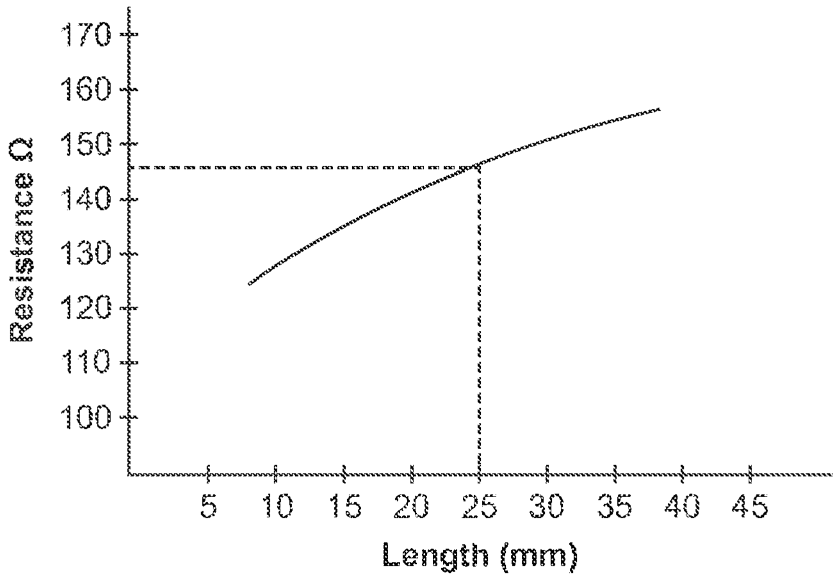
FIG. 1D illustrates a calibration curve for the device of FIGS. 1A-1C.

FIG. 1D illustrates an illustrative calibration curve for the device of FIGS. 1A-IC. As seen in FIG. 1D, an increased resistance corresponds to an increased length of the implantable medical device 12. The calibration curve may be used for a number of different implantable medical devices 12 or it may be tailored to a single implantable medical device 12. In the example of FIG. 1D, a reading of 146Q corresponds to a length of 25.0 mm. Once this conversion has been made the length of 25.0 mm can then be displayed on the display 58 of the controller 52.

Figure 3A:
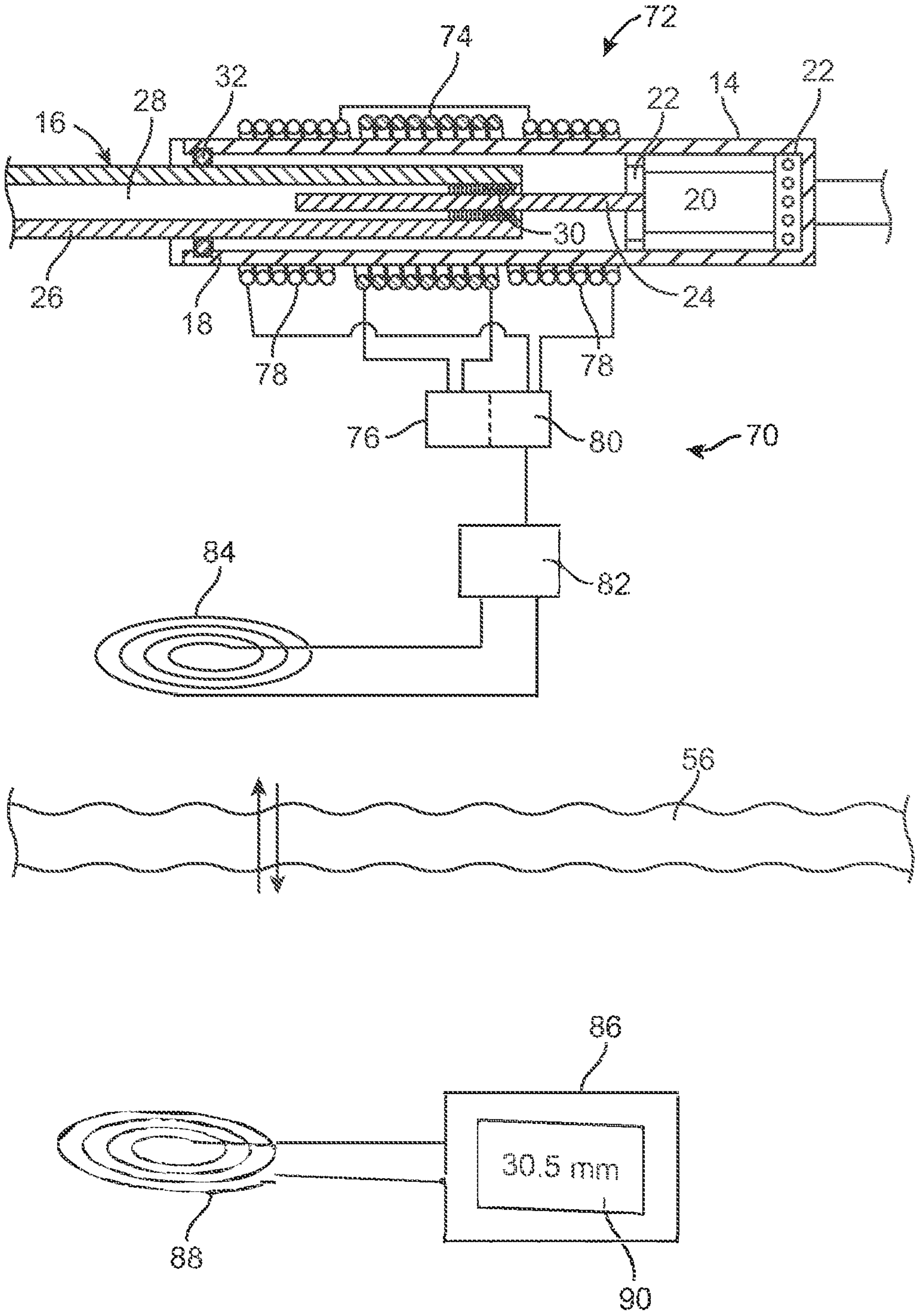
FIG. 3A illustrates a device that non-invasively measures the length of an implantable medical device according to another embodiment.

FIG. 3A illustrates an alternative embodiment of a device 70 that non-invasively measures the length of an implantable medical device 72. The implantable medical device 72 includes a first portion 14 and a second portion 16 that are moveable relative to one another. Those aspects of this embodiment of the implantable medical device 72 that are common with the embodiment of FIGS. 1A-1C are labeled with the same element numbers and will not be described again. In this embodiment, the magnetic coupling between coils is used to measure the length of the implantable medical device 72. In a similar manner to a linear variable differential transformer (LVDT) a primary coil 74 circumscribes the housing 18 and is coupled to a drive circuit 76 that delivers alternating current through the primary coil 74. A secondary coil 78 or multiple secondary coils connected in reverse series also surround the housing 18 and are coupled to a sensing circuit 80 which may be the same as or different from the drive circuit 76. The output signal from the secondary coil(s) 78, which is typically a voltage, is generally proportional to the distance moved by the rod 26 within the housing 18. The location of the primary coil 74 and the secondary coil 78 is such that the coils 74, 78 generally circumscribe the region of overlap between the rod 26 and the housing 18. By measuring the output signal with the secondary coil(s) 78, this value can then be translated into a length of the implantable medical device 72.

The sensed or decoded signal received from the secondary coil(s) 78 is then passed to a telemetry circuit 82. The telemetry circuit 82 wirelessly transmits data through the skin 56 via an antenna 84 to an external controller 86. The external controller 86 is includes an antenna 88 and acts as a receiver to receive data communicated from the telemetry circuit 82. Thus, the telemetry circuit 82 acts as a transmitter while the controller 86 acts as a receiver. In one aspect of the invention, the controller 86 both powers and communicates digitally with the telemetry circuit 82. The controller 86 may also power the sensing circuit 80. In this regard the circuits 80, 82 do not need their own power source as the circuits 80, 82 are powered inductively via the external controller 86. As seen in FIG. 3A, the communication occurs across the skin 56 of the subject.

Figure 3B:
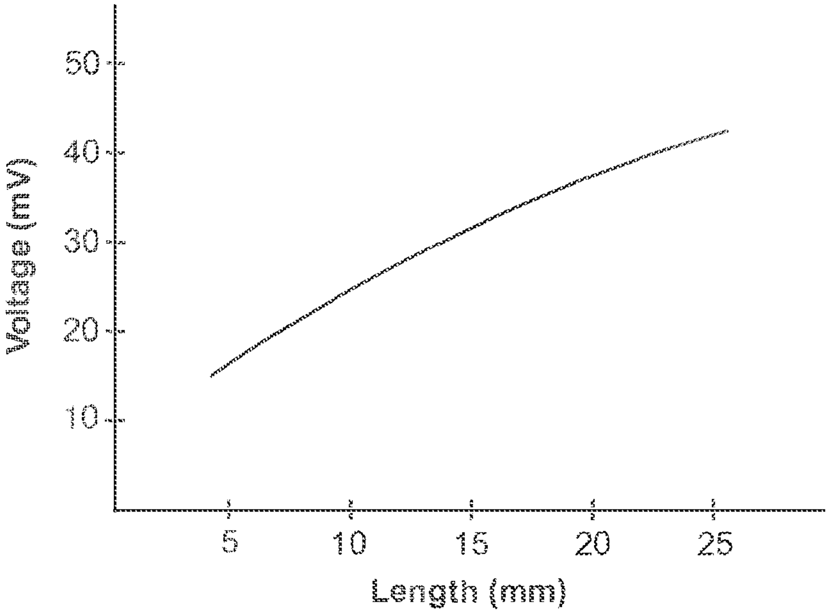
FIG. 3B illustrates a calibration curve for the device of FIG. 3A.

The controller 86, like the controller 52 of the earlier mentioned embodiment, has a display 90 that is used to display length information to a user. In one aspect of the invention, the controller 86 converts the data transmitted by the telemetry circuit 82, which may be voltage data, into length data. The controller 86 may do this by using calibration data that relates the degree of magnetic coupling (e.g., voltage output) to a length. FIG. 3B illustrates an example of a calibration that relates output (voltage) as a function of length. This calibration data may be stored in the controller 86 or transmitted from the telemetry circuit 82. Alternatively, the conversion from magnetic coupling to length can be done by the sensing circuit 80. Regardless of where the conversion is made, once a length is determined, the value can be presented to the user on the display 90.

In this embodiment, the rod 26 acts as a core that affects the degree of magnetic coupling between the primary coil 74 and the secondary coil 78. The rod 26 is preferably made from a material with a relatively high degree of magnetic permeability. This may include metals or alloys of metals. The material should also be biocompatible. Titanium and titanium alloys have excellent biocompatibility and marginal magnetic permeability. To improve on the efficiency of the resulting LVDT, a rod material with a higher magnetic permeability, such as stainless steel or other iron containing materials may be used. If a titanium or titanium alloy rod is desirable, an additional core component with higher magnetic permeability may be attached to the rod. For example a tube may be secured over the outer diameter or within an inner diameter of the rod 26. Alternatively, the nut 30 may be made from a material with higher magnetic permeability than titanium, and thus improve the effect of the core. Generally, the higher degree of magnetic permeability should translate into a device 70 with more sensitivity because an incremental movement of the rod 26 relative to the housing 18 will results in a larger change in magnetic coupling. That is to say, in the context of the calibration curve of FIG. 3B, for a given change in length, a higher degree of magnetic permeability would translate into a larger change in voltage output.

Figure 4A:
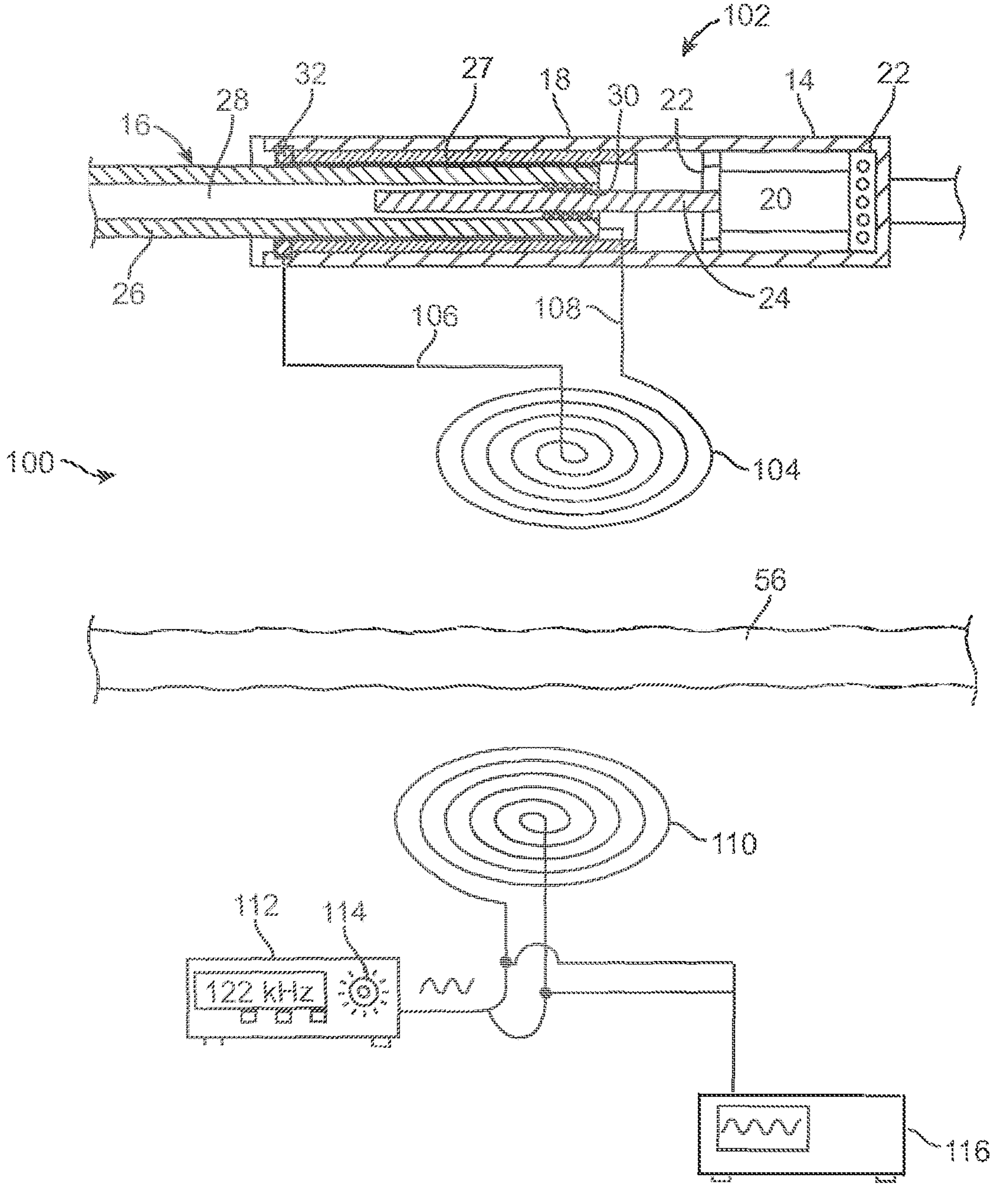
FIG. 4A illustrates a device that non-invasively measures the length of an implantable medical device according to another embodiment.

FIG. 4A illustrates another alternative embodiment of a device 100 that non-invasively measures the length of an implantable medical device 102. The implantable medical device 102 includes a first portion 14 and a second portion 16 that are moveable relative to one another. Those aspects of this embodiment of the implantable medical device 102 that are common with the embodiment of FIGS. 1A-IC are labeled with the same element numbers and will not be described again. In this device 100, a resonant coil 104 is electrically coupled to the housing 18 and the rod 26 via electrical conductors 106, 108. The electrical conductors 106, 108 may include wires, electrical traces in a printed circuit board, or the like. The rod 26 and the housing 18 are electrically isolated from one another. Electrical isolation may be accomplished by preventing the physical touching of the two components. In addition, electrical isolation may be achieved by coating one or both of the rod 26 and housing 18 with a dielectric material. This will isolate the rod 26 from the housing 18 and create a variable capacitor. A dielectric layer 27 between the rod 26 and housing 18 forms a capacitor that varies as the rod 26 moves in and out of the housing 18. The movement of the rod 26 changes the surface area of overlap between the rod and the housing thus changing the capacitance as a function of implant length. When the rod is fully retracted, the capacitance is maximized. When the rod is fully extended, the capacitance is minimized. The dielectric layer 27 may consist of a thin Kapton® (polyimide) tube bonded to the inner diameter of the housing 18, although other dielectric materials may be used (e.g., a gas such as air). Thus, the dielectric layer 27 may be applied as a layer or coating on either the rod 26 or the housing 18 (or both). Alternatively, the dielectric layer 27 may be a gap between the rod 26 and the housing 18 that is filled with air. The resonant coil 104 connected to the capacitor acts as an inductor, creating a resonant LC circuit. The device 100 further includes a drive coil 110 that is coupled to a signal generator 112. The drive coil 110 and signal generator 112 are located external to the subject with the implantable medical device 102 as illustrated in FIG. 4A. The signal generator 112 generates an alternating current (AC) signal that delivered to the drive coil 110. The drive coil 110 is located near or adjacent to the skin 56 of the subject at a location that is near or adjacent to the resonant coil 104. The resonant coil 104 may be located at a location remote from implantable medical device 102 (e.g., near the surface of the skin 56). The signal generator 112 preferably has the ability to deliver AC signals to the drive coil 110 at a variety of frequencies via input 114. The device 100 further includes a frequency analyzer 116 which may take the form of an oscilloscope or the like. The frequency analyzer 116 is used to determine when the resonant frequency of the implantable medical device 102 has been reached. In particular, the frequency of the applied AC signal is adjusted via the signal generator 112 until the frequency analyzer 116 detects that the resonant frequency has been reached. The frequency range sweep by the signal generator 112 may be automated or even manual. Detection is made when the amplitude of the signal detected by the frequency analyzer 116 drops or dips significantly. This may be detected automatically by the frequency analyzer 116. The user will thus know the resonant frequency of the implantable medical device 102 which can then be converted to a length. The particular resonant frequency of the implantable medical device 102 varies as a function of the length. A calibration curve that includes the resonant frequency of the implantable medical device 102 as a function of length can then be used determine the absolute length of the implantable medical device 102. In this regard, once the user knows the resonant frequency, the corresponding length value can be determined using the calibration curve. This can be done manually or it could be automated using a processor or computer that translates the measured resonant frequency into a length value. The frequency analyzer 116 may be separate from the signal generator 112 as seen in FIG. 4A, however, in other embodiments these two components may be integrated into a single external device as seen in FIG. 4C.

Table 1 listed below illustrates data obtained generating a calibration curve of an implantable medical device 102. Data was obtained by varying the length of the implantable medical device 102 in ¼ inch increments and adjusting the frequency of the signal generator 112 until the resonant frequency was observed with the frequency analyzer 116. In the tested device, 0.0025 inch KAPTON® polyimide tape was wrapped around the rod 26 to isolate it from the housing 18 and act as a dielectric. As noted above, the resonant frequency was determined based on a dip of the amplitude of the signal measured by the frequency analyzer

TABLE 1

| Distraction (inches) | Resonant Frequency (kHz) |
|---|---|
| 0 | 104.016 |
| .25 | 110.083 |
| .50 | 116.780 |
| .75 | 123.887 |
| 1.00 | 133.136 |
| 1.25 | 141.557 |
| 1.50 | 153.635 |
| 1.75 | 168.469 |
| 2.00 | 190.366 |

Figure 4B:
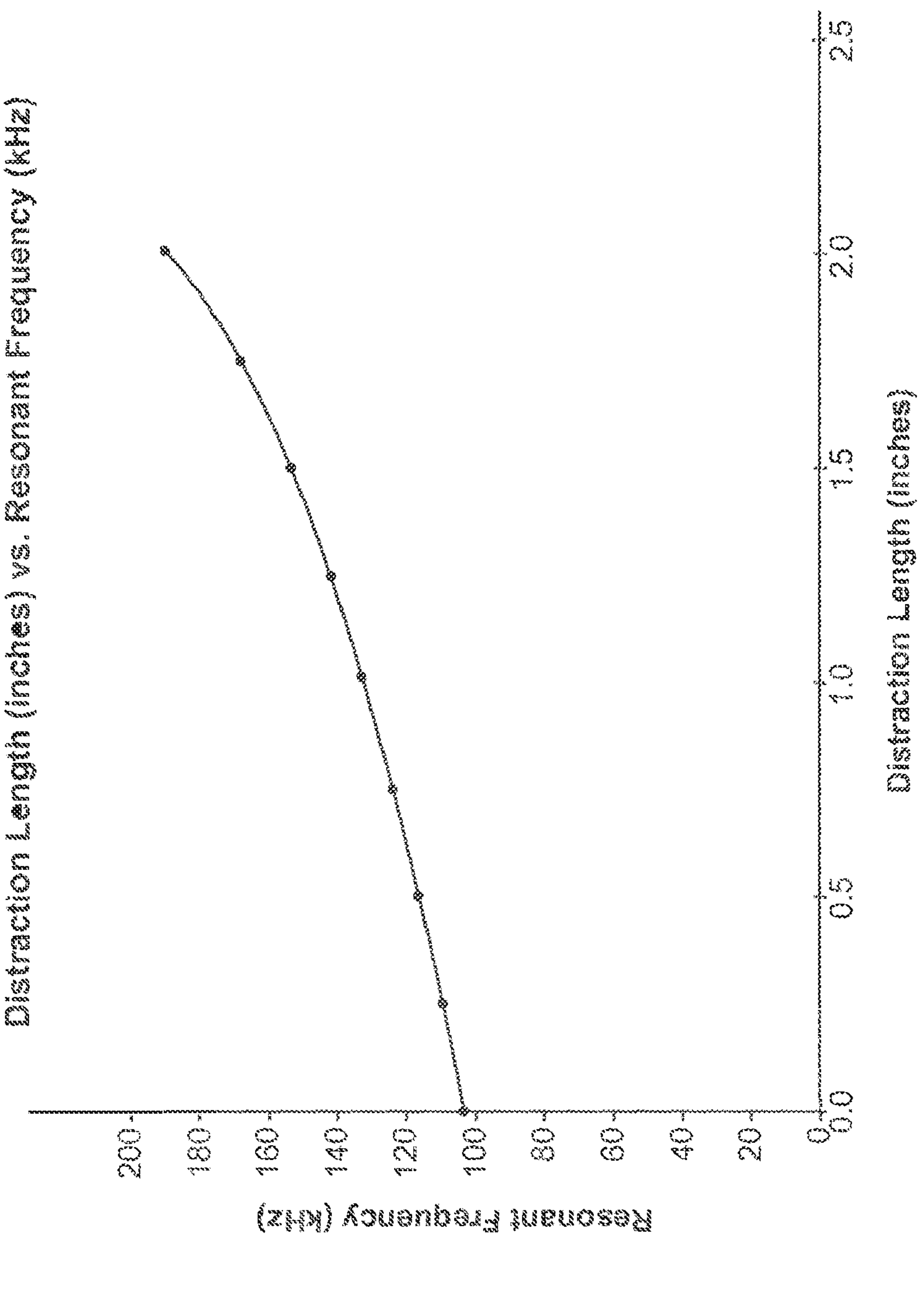
FIG. 4B illustrates a calibration curve for the device of FIG. 4A.
Figure 4C:
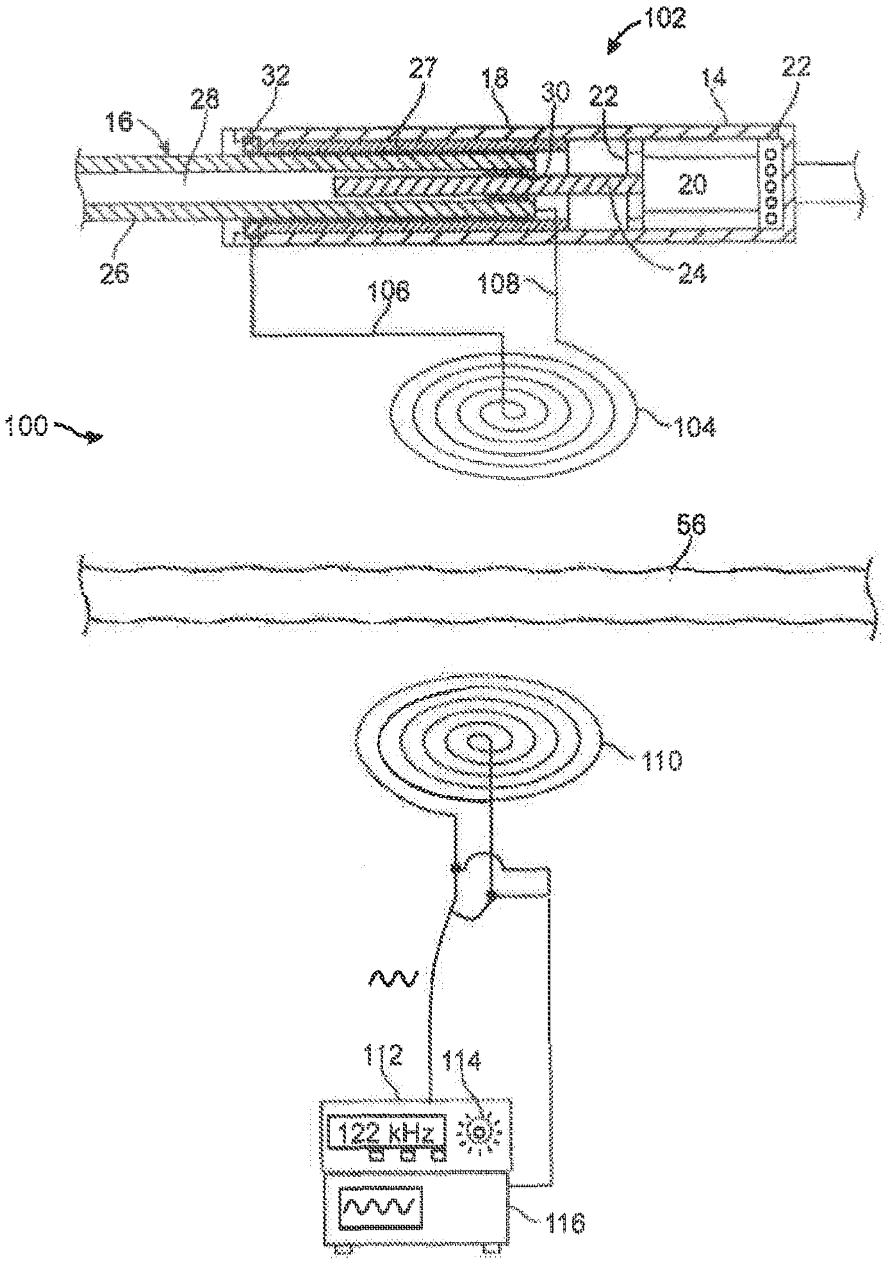
FIG. 4C illustrates another embodiment of the device of FIG. 4A.

FIG. 4B illustrates the data of Table 1 plotted as a calibration curve showing distraction length as function of resonant frequency. In this embodiment, once the resonant frequency is determined, one can then readily determine the distraction length based on the calibration curve. The calibration curve may be unique to the implantable medical device 102 and may be provided with the same or the calibration curve can be developed by the physician. Again, this method enables the physician or other skilled person to determine the absolute length of the implantable medical device 102 by non-invasive interrogation.

Figure 5A:
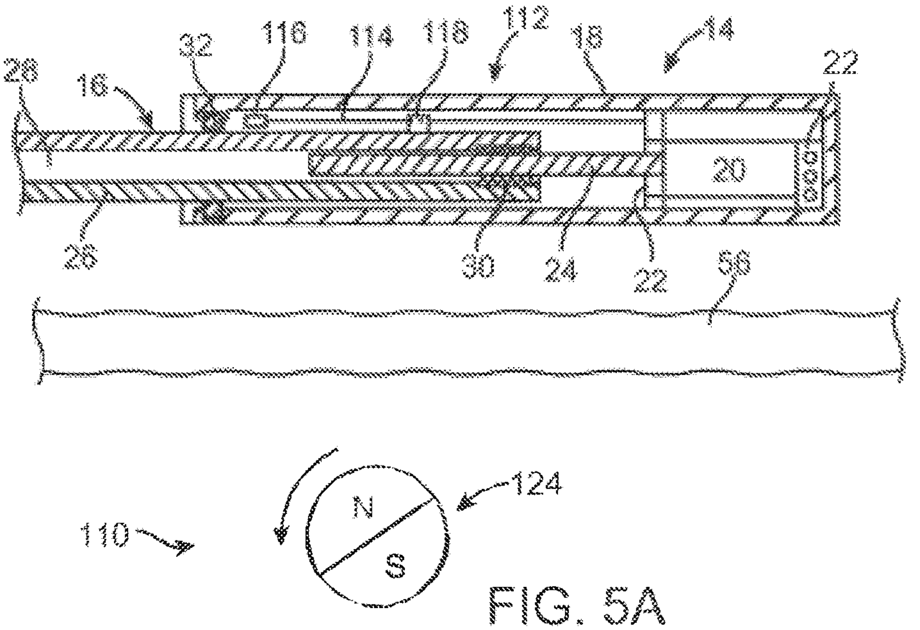
FIG. 5A illustrates a device that non-invasively measures the length of an implantable medical device according to another embodiment.
Figure 5B:
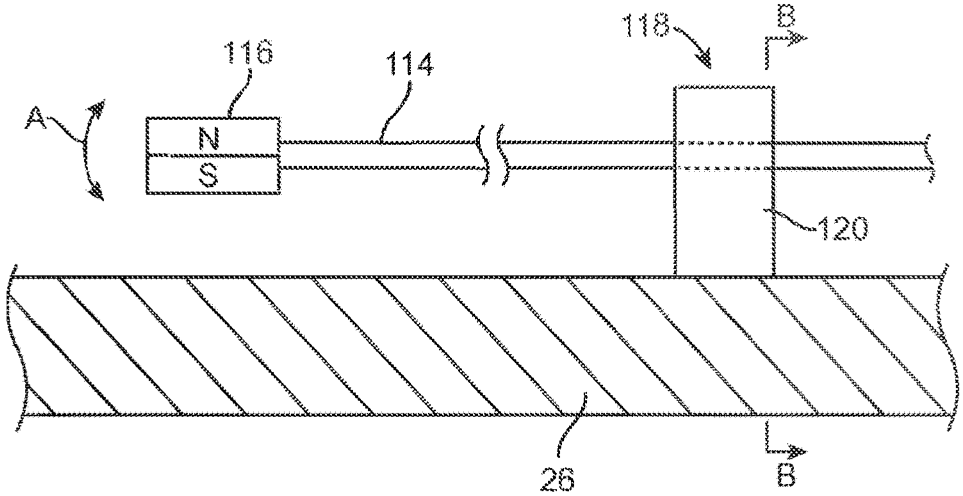
FIG. 5B illustrates an enlarged view showing the rod and fulcrum that interfaces with the elongate member having a magnet disposed on an end thereof.
Figure 5C:
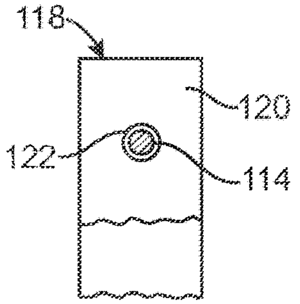
FIG. 5C illustrates a cross-sectional view taken along the line B-B of FIG. 5B.

FIGS. 5A-5E illustrate another alternative embodiment of a device 110 that non-invasively measures the length of an implantable medical device 112. The implantable medical device 112 includes a first portion 14 and a second portion 16 that are moveable relative to one another. Those aspects of this embodiment of the implantable medical device 102 that are common with the embodiment of FIGS. 1A-IC are labeled with the same element numbers and will not be described again. As best seen in FIGS. SA and 5B, an elongate member 114 is disposed inside the housing 18 and is affixed to the housing 18 at one end thereof. On the opposing end of the elongate member 114 is located a permanent magnet 116 (best seen in FIG. 5B). The elongate member 114 passes through a fulcrum 118 that is fixedly attached to the rod 26. As best seen in FIGS. 5B and 5C, the fulcrum 118 may include a projection 120 extending from the rod 26 that includes an aperture 122 dimensioned to permit the fulcrum 118 to slide along the length of the elongate member 114 as the rod 26 is moved relative to the housing 18. In this regard, the fulcrum 118 adjusts the length of the elongate member 114 between the magnet 116 and the fulcrum 118. By changing this length, the natural vibrational frequency of the elongate member 114 changes.

Figure 5D:
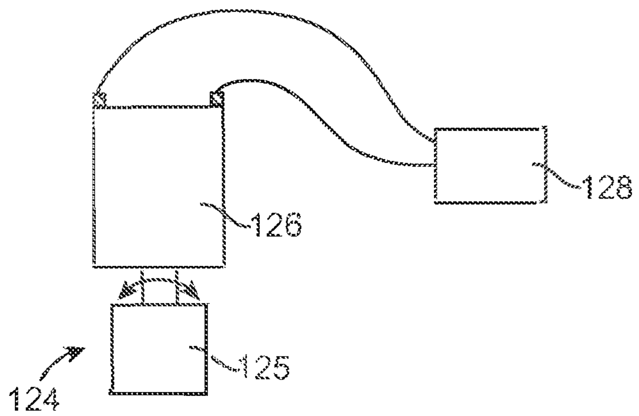
FIG. 5D illustrates a motor driven external magnet for use with the device of FIG. 5A.
Figure 5E:
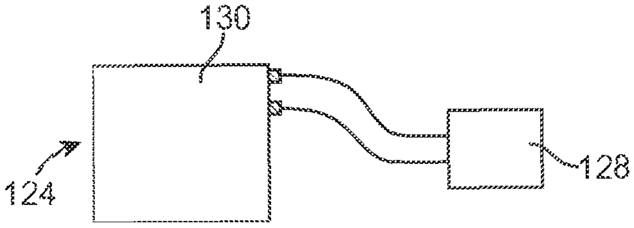
FIG. 5E illustrates an external electromagnet for use with the device of FIG. 5A.
Figure 5F:
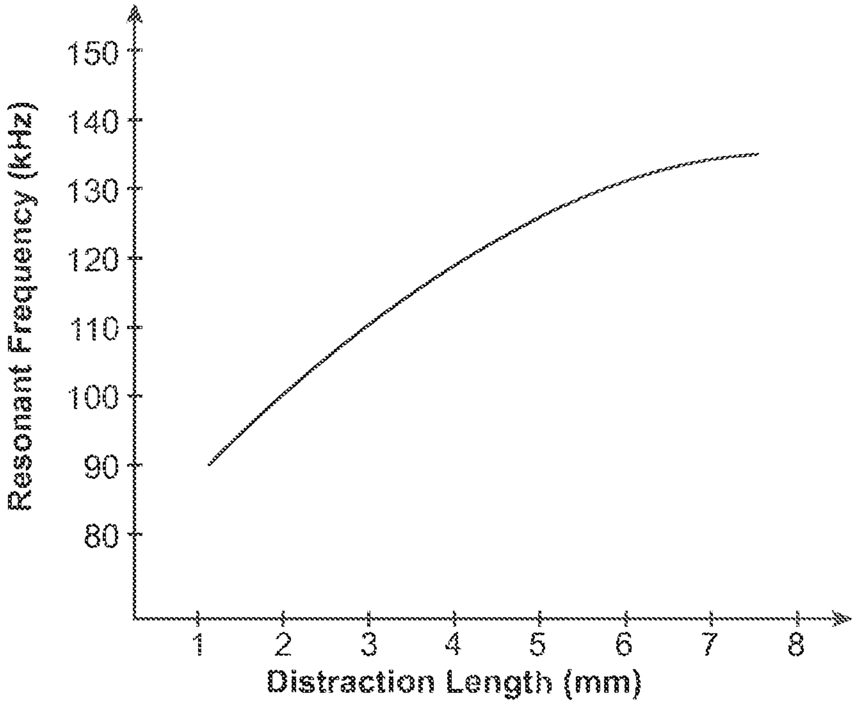
FIG. 5F illustrates a calibration curve for the device of FIG. 5A.

As part of the device 110, an externally located magnetic field source 124 is provided that applies an oscillating magnetic field to the implantable medical device 112. The oscillating magnetic field passes through the skin 56 of the subject and interacts with the magnet 116 disposed on the end of the elongate member 114. During use, the frequency of the oscillating magnetic field is adjusted (e.g., step wise adjustment) until the resonant frequency of the elongate member 114 is reached. At the resonant frequency, the magnet 116 and attached elongate member 114 vibrate back-and-forth as illustrated by arrow A of FIG. 5B. This vibration can be detected by the power that is supplied to magnetic field source 124. In one aspect, as seen in FIG. 5D, the magnetic field source 124 is a permanent magnet 125 that is rotated by a motor 126 that is powered by a driving circuit 128. The driving circuit 128 is capable of adjusting the rotational frequency of the motor 126 and thus the magnet 125. The driving circuit 128 is also able to monitor the current that drives the motor 126 using current sense circuitry. The resonant frequency is detected when a current spike is observed in the driving circuit 128. The frequency of the oscillating magnetic field can then be converted to a device length by using a calibration curve that relates length of the device to the rotational frequency of the oscillating magnetic field. FIG. 5F illustrates an exemplary calibration curve of the resonant frequency as a function of length for the device 110. The length of the device 110 may be determined by examining where the resonant frequency intersects with the calibration curve. As with all the calibration curves described herein, this may be done as a look-up table, function, or other method commonly known to those skilled in the art. As an alternative to the use of the motor 126, FIG. 5E illustrates an alternative embodiment that uses an electromagnet 130 that is driven by a driving circuit 128. Driving current can be measured by current sense circuitry in the driving circuit 128.

While embodiments have been shown and described, various modifications may be made without departing from the scope of the inventive concepts disclosed herein. For example, while the devices described in detail herein are driven non-invasively, the methods and devices are also applicable to implantable medical device that are adjusted manually. Similarly, while embodiments described in detail herein utilize a magnet coupled to a lead screw to adjust the length of an implantable medical device other drive devices may fall within the scope of the invention. Moreover, only a portion of the implantable medical device may change length or shape and be measured in a non-invasive manner. The invention(s), therefore, should not be limited, except to the following claims, and their equivalents.

What is claimed is:

1. A method of sensing the length of an implantable medical device comprising:

providing an implantable medical device, the implantable medical device including:

a first portion secured to a first bone and a second portion moveable relative to the first portion and secured to a second bone, the first portion includes a housing including a rotatable magnet, and a threaded lead screw coupled to the rotatable magnet, and the second portion includes a rod having a threaded nut interfacing with the threaded lead screw, such that rotation of the rotatable magnet rotates the lead screw to cause telescopic movement of the second portion into the first portion;

an elongate member having first and second ends, the first end being secured to the first portion of the implantable medical device, the second end secured to a magnet, and a fulcrum on the second portion of the implantable medical device and in contact with various points along the elongate member in response to relative movement of the second member relative to the first member;

applying an oscillating magnetic field at different frequencies in proximity to the magnet with an externally located magnetic field source driven by a power source;

monitoring, using a computer, the power source for the externally located magnetic field source; and calculating, using the computer, the resonant frequency of the elongate member based at least in part on the current draw of the power source; and converting, using the computer, the resonant frequency of the elongate member to a length value of the implantable medical device.

2. The method of claim 1, wherein the externally located magnetic field source includes a rotatable permanent magnet operatively connected to a motor.

3. The method of claim 2, wherein current sense circuitry is operatively coupled to the motor.

4. The method of claim 1, wherein the externally located magnetic field source includes an electromagnet.

5. The method of claim 4, wherein a current sense circuitry is operatively coupled to the electromagnet.

6. The method of claim 1, wherein the elongate member extends through the fulcrum.

7. The method of claim 1, wherein the fulcrum includes a projection extending from the second portion.

8. The method of claim 1, wherein the projection includes an aperture dimensioned to permit the fulcrum to slide along a length of the elongate member.

9. The method of claim 1, wherein the calculating of the resonant frequency includes detecting a current spike observed in a driving circuit of the externally located magnetic field source.

10. The method of claim 1, wherein a seal is disposed between the first portion and the second portion.

11. A method of sensing the length of an implantable medical device comprising:

providing an implantable medical device, the implantable medical device including:

a first portion and a second portion telescopically moveable relative to one another, an elongate member having first and second ends, the first end being secured to the first portion of the implantable medical device, the second end secured to a magnet, and a fulcrum on the second portion of the implantable medical device and in contact with various points along the elongate member in response to relative movement of the second member relative to the first member;

applying an oscillating magnetic field at different frequencies in proximity to the magnet with an externally located magnetic field source driven by a power source;

monitoring, using a computer, the power source for the externally located magnetic field source; and calculating, using the computer, the resonant frequency of the elongate member based at least in part on the current draw of the power source; and converting, using the computer, the resonant frequency of the elongate member to a length value of the implantable medical device, wherein the first portion includes a housing having a first closed end configured to be secured to a first portion of a bone and a second open end opposite the first closed end, and a lead screw within the housing that extends along a central axis of the housing and is rotatably secured to a rotatable magnet, such that rotation of the rotatable magnet rotates the lead screw to cause telescopic movement of the second portion into the first portion, wherein the second portion includes a rod having a first closed end configured to be secured to a second portion of the bone, a hollow segment dimensioned to receive the lead screw, and a second open end opposite to the first closed end of the rod having a threaded nut configured to engage the lead screw within the hollow segment.

12. The method of claim 11, wherein the externally located magnetic field source includes a rotatable permanent magnet operatively connected to a motor.

13. The method of claim 12, wherein current sense circuitry is operatively coupled to the motor.

14. The method of claim 11, wherein the externally located magnetic field source includes an electromagnet.

15. The method of claim 14, wherein a current sense circuitry is operatively coupled to the electromagnet.

16. The method of claim 11, wherein the elongate member extends through the fulcrum.

17. The method of claim 11, wherein the fulcrum includes a projection extending from the second portion.

18. The method of claim 11, wherein the projection includes an aperture dimensioned to permit the fulcrum to slide along a length of the elongate member.

19. The method of claim 11, wherein the calculating of the resonant frequency includes detecting a current spike observed in a driving circuit of the externally located magnetic field source.

20. The method of claim 11, wherein a seal is disposed between the rod and the housing.

* * * * *